United States Patent [19]

Goldberg

[11] Patent Number: 5,260,871
[45] Date of Patent: Nov. 9, 1993

[54] METHOD AND APPARATUS FOR DIAGNOSIS OF BREAST TUMORS

[75] Inventor: Victor Goldberg, Mendota Heights, Minn.

[73] Assignee: Mayo Foundation for Medical Education and Research, Rochester, Minn.

[21] Appl. No.: 738,460

[22] Filed: Jul. 31, 1991

[51] Int. Cl.$^5$ .................. G06F 15/00; G06K 9/62
[52] U.S. Cl. .................. 364/413.02; 364/413.01; 364/413.13; 382/15; 382/36
[58] Field of Search .............. 364/413.08, 413.01, 364/413.13, 413.02, 413.14, 513; 382/56, 15, 16, 36, 6

[56] References Cited

U.S. PATENT DOCUMENTS 4,965,725 10/1990 Rutenberg .................. 364/413.1

OTHER PUBLICATIONS

R. P. Lippmann, "An introduction to computing with neural nets," IEEE ASSP Magazine, pp. 4-22 (Apr. 1987).
D. E. Rumelhart, G. E. Hinton, and R. J. Williams, "Learning internal representation by error propagation," *Parallel Distributed Processing*, D. E. Rumelhart, McClelland and the PDP Research Group Editors (The MIT Press, 1986).
P. D. Wasserman, *Neural Computing, Theory and Practice* (Van Nostrand Reinhold, pp. 43-58, 1989).
V. Goldberg et al., "Improvement in specificity of ultrasonography for diagnosis of breast tumors by means of artificial intelligence," Mayo Clinic and Mayo Foundation (1990).
J. J. Gisvold, "Imaging of the breast: Techniques and results," Mayo Clinic Proc. 65, 56-66 (1990).
V. Goldberg, J. J. Gisvold, T. M. Kinter, and J. F. Greenleaf, "Textue analysis of ultrasound B-scans to aid diagnosis of cancerous lesions in the breast," 1988 Ultrasonics Symposium, pp. 839-842 (1988).
M. M. Galloway, "Texture analysis using gray level run lengths," Computer Graphics and Image Processing 4, 172-179 (1975).
N. J. Pressman, "Markovian analysis of cervical cell images," J. of Histochem. and Cytochem. 24, 138-144 (1976).
R. A. Robb, "Multidimensional biomedical image display and analysis in the Biotechnology Computer Resource at Mayo Clinic," Machine Vision and Applications 1, 75-96 (1988).
S. Finette, A. Bleier, and W. Swindell, "Breast tissue classification using diagnostic ultrasound and pattern recognition techniques: I. Method of pattern recognition," Ultrasonic Imaging 5, 55-70 (19803).

*Primary Examiner*—Roy N. Envall, Jr.
*Assistant Examiner*—Frantzy Poinvil
*Attorney, Agent, or Firm*—Merchant, Gould, Smith, Edell, Welter & Schmidt

[57] ABSTRACT

An apparatus for distinguishing benign from malignant tumors in ultrasonic images of candidate tissue taken from a patient. A region of interest is located and defined on the ultrasonic image, including substantially all of the candidate tissue and excluding substantially all the normal tissue. The region of interest is digitized, generating an array of pixels intensity values. A first features is generated from the arrays of pixels corresponding to the angular second moment of the pixel intensity values. A second feature is generated from the array of pixels corresponding to the inverse contrast of the pixel intensity values. A third feature is generated from the array of pixels corresponding to the short run emphasis of the pixel intensity values. The first, second and third feature values are provided to a neural network. A set of trained weights are applied to the feature values, which generates a network output between 0 and 1, whereby the output values tend toward 1 when the candidate tissue is malignant and the output values tend toward 0 when the candidate tissue is benign.

6 Claims, 6 Drawing Sheets

$d = O \bullet w$

Fig. 6
Data Path and Procedure

METHOD AND APPARATUS FOR DIAGNOSIS OF BREAST TUMORS

BACKGROUND OF THE INVENTION

1. Field of the Invention

The present invention relates to a method and apparatus for improved diagnosis of breast tumors using computer vision and neural network image processing.

2. Description of the Background Art

The demand for screening mammography has substantially increased in the last 10 years. For example, the Mayo Clinic has experienced an increase in volume from fewer than 10,000 mammograms in 1979 to more than 36,000 in 1989. Based on statistics maintained at the Mayo Clinic for the years 1986 to 1988, mammography failed to detect 4% of the cancers removed surgically. Malignancy was found in 25% of all surgical biopsies performed after a wire localization procedure. A benign pathologic result was noted for 75% of these patients. Further, the 4% false-negative negative rate for detecting cancer cannot be equated to sensitivity. True sensitivity can only be determined by continued follow-up with the patient.

In current radiologic practice, ultrasound is used as a tool to improve the specificity and sensitivity of total breast imaging. Sensitivity is the ability to identify malignant tumors divided by the total population of patients with the malignancy. Specificity is the ability to identify benign tumors divided by the total population of patients with benign tumors. Although both sensitivity and specificity are important, it is preferable to miscategorize patients as a false positive, rather than a false negative.

When the radiologist arrives at an indeterminate diagnosis based on the reading of a mammogram, ultrasound imaging of the lesion probably will be done as an intermediate step between mammography and biopsy if the lesion in question is a palpable mass, a mammographic mass, or both. If ultrasonography reveals a cyst, no excisional biopsy is recommended. Otherwise, if an indeterminate tumor is diagnosed, a biopsy is usually, but not always, recommended.

A cyst is a collection of liquid that usually is seen on ultrasonographic examination as a well-circumscribed lesion with no internal echoes, and increased through-transmission of sound. Cysts are considered benign lesions.

Occasionally, malignant lesions can have mainly cyst-like characteristics on ultrasonographic examination. A malignant cystic-like lesion can easily be incorrectly diagnosed as benign. The present state-of-the-art of breast ultrasound attempts to distinguish between cystic and solid lesions. However, using current ultrasonographic criteria, solid lesions are indeterminate.

SUMMARY OF THE INVENTION

The present invention performs a texture analysis of images generated by an ultrasound system. A number of techniques are used to compare the intensities of the picture elements (pixels) with the intensities of their neighbors on a digitized ultrasonogram. These measurements are reduced to features which are fed into the neural network, which applies weighted inputs to classify the tumor as malignant or benign.

The neural network must be trained prior to use. The desired outputs for given inputs are compared with actual outputs and adjustments are made to the network's weights based on the differences. This process is repeated for many presentations of many inputs until the network produces the desired responses. When difference between the desired output and the actual output converge, the network is trained and can be used for test sets. A set of ultrasonograms of lesions from 200 patients between the ages of 14 and 93 years who underwent mammography followed by ultrasonographic examination and excisional biopsy were used as learning data (i.e., feature and target data) to train the neural network of the present invention. The preferred and illustrated texture analysis methods of the present invention are used to generate "short run emphasis" and the Markov features of "angular second moment" and "inverse contrast". These features are then fed into the neural network which performs the classifying function.

The present invention includes a "gap" technique which biases the network toward correctly classifying all the malignant cases at the expense of some misclassification of the benign cases, thereby diagnosing these cases with 100% sensitivity and 40% specificity (compared with 0% specificity for the radiologists diagnosing the same set of cases in the breast imaging setting), thus suggesting the possibility of decreasing the number of unnecessary biopsies by 40%.

DESCRIPTION OF THE PREFERRED EMBODIMENT

Figure 1A:
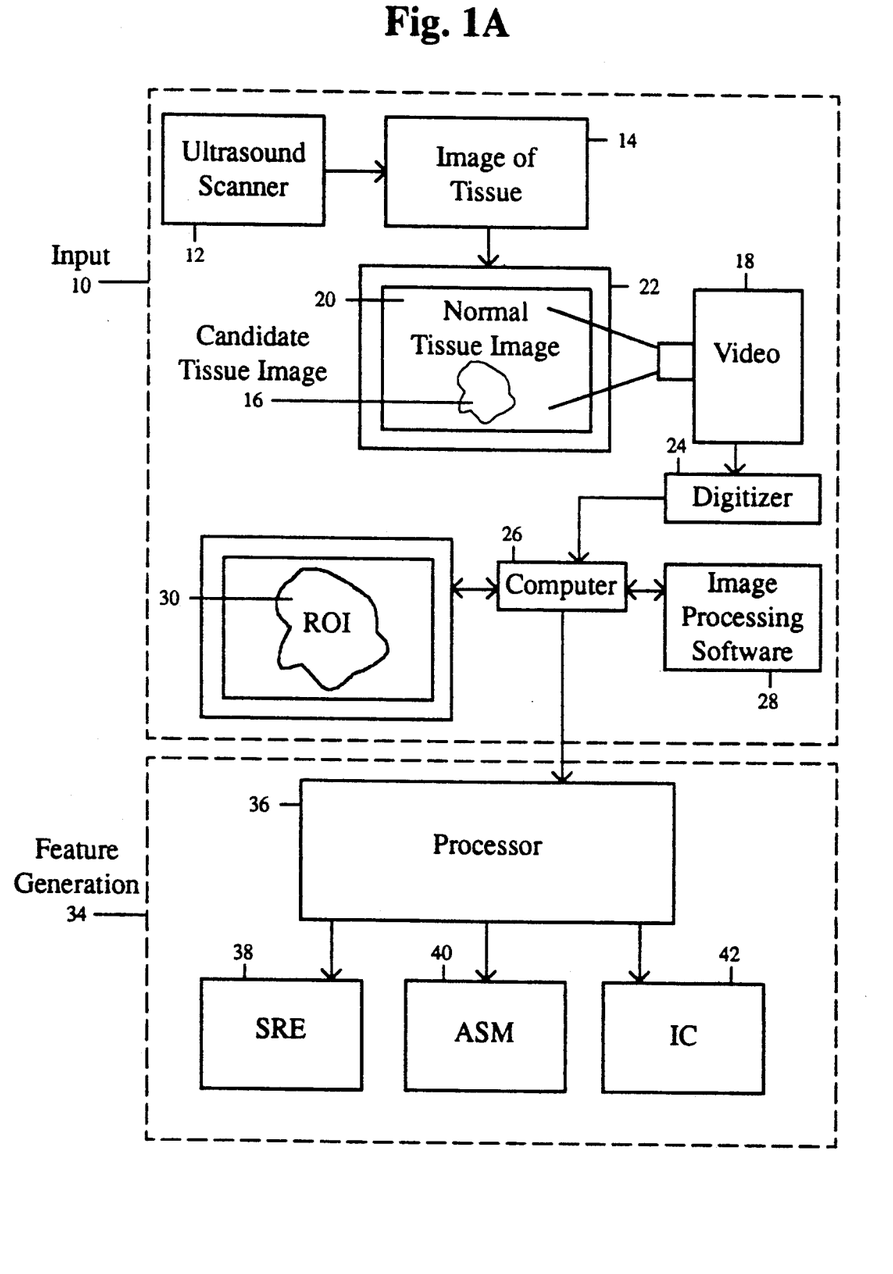
FIGS. 1A and 1B are a schematic block diagram depicting the hardware and software of the breast tumor diagnostic system of the present invention.

FIG. 1A illustrates the breast tumor diagnostic system of the present invention. Data input 10 into the neural network begins with an ultrasonographer, and usually a radiologist, scanning the patient using a scanner 12. The scanning process is directed by the mammographic appearance or palpation, or both, regarding the location of the lesion. The preferred embodiment of the present invention utilizes a 7.5-MHz Ausonics ® scanner.

A representative image 14 of the tissue is recorded on film for later study by the radiologist. The film image 14 that shows the largest and best defined view of the candidate tissue 16 with the least amount of normal tissue 20 is converted to digitized image 22 by a video camera 18. It should be noted that when digitizing data from film, variations of developing conditions as well as variations in the film itself can significantly affect the image texture. Image texture is also affected by the video digitation process, and care must be taken to preserve image quality at all steps in the process.

In the digitizing step, the film 14 is placed on a light box (not shown) and an RCA TC1005/x01 video camera is focused on the chosen film frame in such a way that the frame occupied a maximal area of the screen of a monitor connected to the camera output. Once an optimum or optimal image magnification is established, it is held constant for all patients, to preserve uniformity of image texture.

The output of the video camera 18 is connected to a digitizer 24, which collects the image in a format that can be processed by a computer 26. The preferred embodiment utilizes a Grinnel GMR 27 series digitizer. Eight bits per pixel are used to describe intensity and the 512×512 image, with a scale of 5.54 pixels per mm. Vertically, only the first 480 rows contained image information.

Image processing software 28 called ANALYZE is used to view the digitized image 20 and to extract a region of interest (ROI) 30 by hand tracing, using the SLICE EDIT function. The ROI 30 is chosen to include as much candidate tissue 16 as possible, without including normal tissue 22. Any tissue outside the ROI is ignored during subsequent processing.

The tumors are characterized to a large extent by being hypoechoic relative to the surrounding tissue, which means that on most occasions the dynamic range of the ROI 30 is quite limited with respect to the available scale. In most cases the intensities of the echoes from inside the tumors are low and use mostly the lower half of the available scale.

Figure 2:
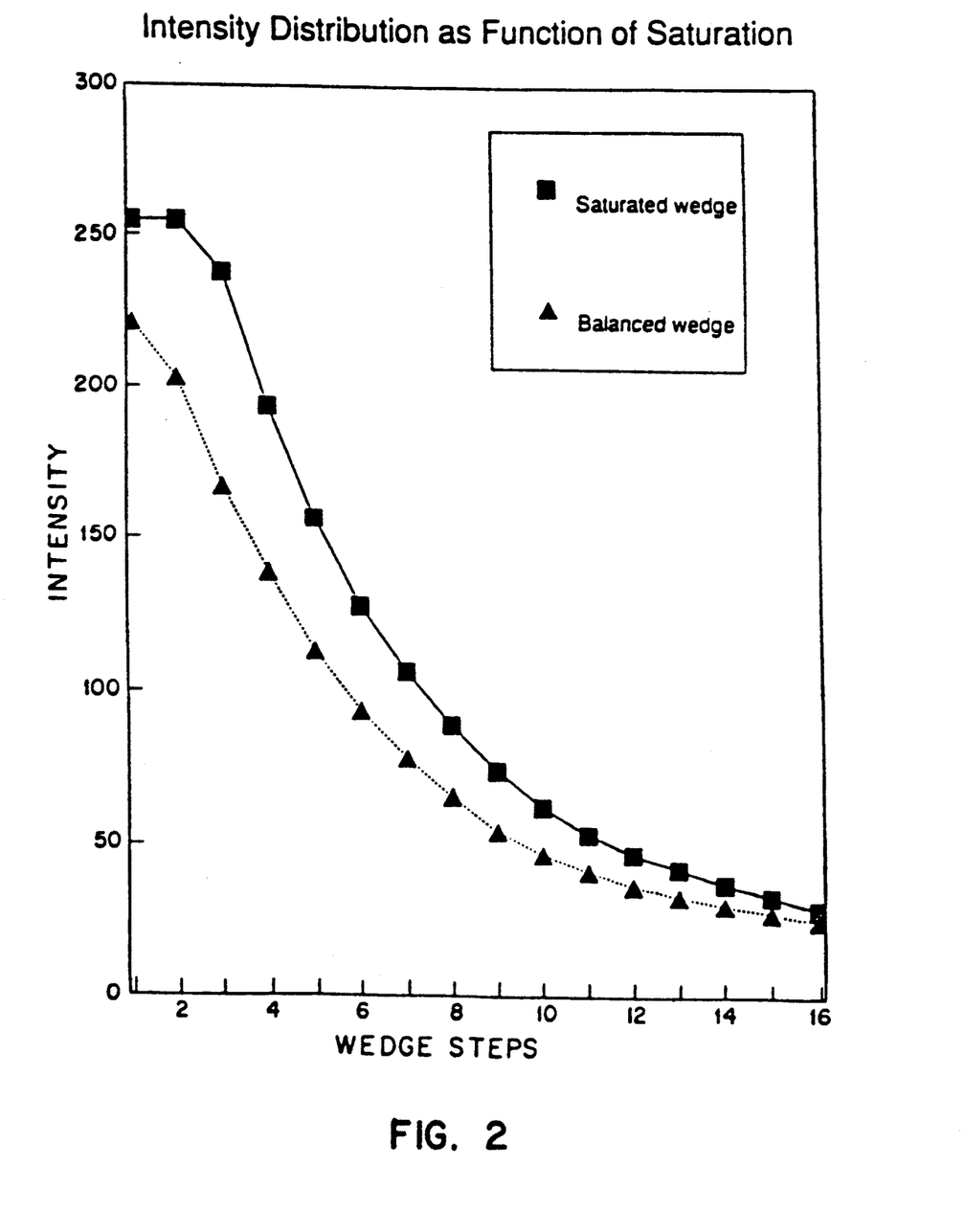
FIG. 2 is a graphic description of the gray level distribution of pixels before and after saturation of the present invention.

In order to increase the dynamic range, the image data is slightly saturated during digitizing. To do this in a quantitatively consistent way, the video camera 18 output is calibrated with a gray scale wedge. The calibration criterion used is that the two highest intensity steps of the wedge are saturated, thereby increasing the dynamic range of the lower half of the scale and emphasizing the candidate tissue. A histogram of the wedge is shown in FIG. 2. The primary purpose of this procedure is to increase contrast in the region of interest. If the digitizations are done in more than one session, the same calibration criterion can be used in subsequent sessions.

Feature Generation

To decrease the decision-making process to a binary procedure, the different tumors are considered as separate classes, malignant and benign tumors being complementary classes. The purpose of feature generation 34, illustrated in FIG. 1A, is to extract from each digitized ROI 30 a small set of numbers that would characterize the image as belonging to the benign class or the malignant class. The features generated in the present invention are based on the texture analysis of the ultrasonograms of the candidate tissue.

A processor 36 performs the feature generation 34, as well as the design, training and testing of the neural network. Training and testing in the preferred embodiment of the present invention utilizes the NeuralWorks® Professional II software program on a Sun Sparcstation® I. It will be appreciated that the image processing performed by the computer 26 could be performed by the processor 36.

Feature generation 34 utilizes run length and Markovian techniques in the preferred embodiment of the present invention. These techniques rely on the creation of intermediary matrices whose elements describe relationships between intensities of neighboring pixels. These matrices are then reduced to sets of single numbers according to certain rules that use all the elements in the intermediary matrix. Each specific rule, also called a "feature," generates one number per image.

Run length features are based on the measurement of the length of strings of pixels with similar intensity values, whereas Markovian features are based on the variation of intensities between neighboring pixels at various distances. Both techniques are discussed in more detail below. Using these techniques, about 30 features are produced. The numeric values of several features describing a candidate tissue are used to characterize it as either benign or indeterminate. To grade the individual features in relation to their relative quality as classifiers, the numeric values of each feature for all the cases are sorted and tabulated against the tag of each case as benign or malignant. The features that had the largest number of cases at one end of their own scale that are solely benign (no mixture of benign and malignant cases) are considered the best classifying individual features. Pairs of features are plotted on a plane in feature space, and their classifying potential is evaluated. An artificial neural network classifier, discussed in detail below, classifies the sets according to more than two features.

The larger the number of meaningful features used, the better the classification of the sample. However, the robustness or ability to generalize to larger populations is improved by decreasing the number of features used for classification. A way to test robustness is by application of the method to a different sample of data. The acceptable ratio between the size of the smallest class and the dimensionality of the classifying feature space generally accepted in the literature varies between 3 and 20. A ratio of about 10 was selected for the preferred embodiment of the present invention.

Three features were selected from 34 sample malignant cases in the preferred embodiment of the present invention. The features chosen were the angular second moment (ASM) 40, the inverse contrast (IC) 42, both from the Markov family, and the short run emphasis (SRE) 38 from the run length family.

Run Length Method: Short Run Emphasis (SRE)

A gray-level run is a set of consecutive collinear pixels belonging to the same predefined range of gray-level values. The length of the run is the number of pixels in the run. For a given image, a gray-level run length table can be built for runs in any given direction. The table elements (i, j) specifies the number of times that the image contains a run of length j, in the given direction, consisting of pixels in gray-level range i. Many rules can be applied to decrease such a table to a single number. One such rule (also called feature) that was found useful for diagnostic purposes is called short run emphasis (SRE) 38, $$sre = \frac{\sum_{i=1}^{N_g} \sum_{j=1}^{N_r} \frac{p(i,j)}{j^2}}{\sum_{i=1}^{N_g} \sum_{j=1}^{N_r} p(i,j)}$$

where p(i,j) is the (i,j)th entry in the given run length matrix, $N_g$ by $N_r$).

The name of this feature comes from the fact that each run value is divided by its length squared, emphasizing the short runs.

Markovian Method: Angular Second Moment (ASM) and Inverse Contrast (IC)

From the data of a digitized image, a table of gray-level transition probability values can be extracted for a step size L, $$\begin{matrix} P_L(0,0) & P_L(0,1) & \ldots & P_L(0,N) \\ P_L(1,0) & P_L(1,1) & \ldots & P_L(1,N) \\ \cdot & \cdot & & \cdot \\ \cdot & \cdot & & \cdot \\ \cdot & \cdot & & \cdot \\ P_L(N,0) & P_L(N,1) & \ldots & P_L(N,N) \end{matrix}$$

in which each element is defined as the probability of gray level i occurring L pixels after gray level j occurs. As in the case of run length, many rules can be applied to decrease this table to a single number. Two such features found to be useful for classification purposes are the angular second moment (ASM) 40 and the inverse contrast (IC) 42.

$$asm = \sum_{i=1}^{N} \sum_{j=1}^{N} [P_L(i,j)]^2$$

$$ic = \sum_{n=1}^{N-1} \left[ \frac{\sum_{i=1}^{N} \sum_{j=1}^{N} P_L(i,j)}{n} \right]_{|i-j|=n}$$

The present invention calculates the rules for steps L between 1 and 10 as well as the variation between steps as different features. There is a certain similarity between the SRE 38 and the IC 42 features in the sense that both increase in value when neighboring pixels are similar. However, the two-dimensional space defined by these features allows for better classification than does either feature separately.

Neural Networks

Neural networks are alternative computing models based on simple "neuron-like" processing elements and their interactions. Methods based on these models show promise for many applications, and the back propagation model in particular has been well-studied and successfully applied to various classification problems.

Figure 1B:
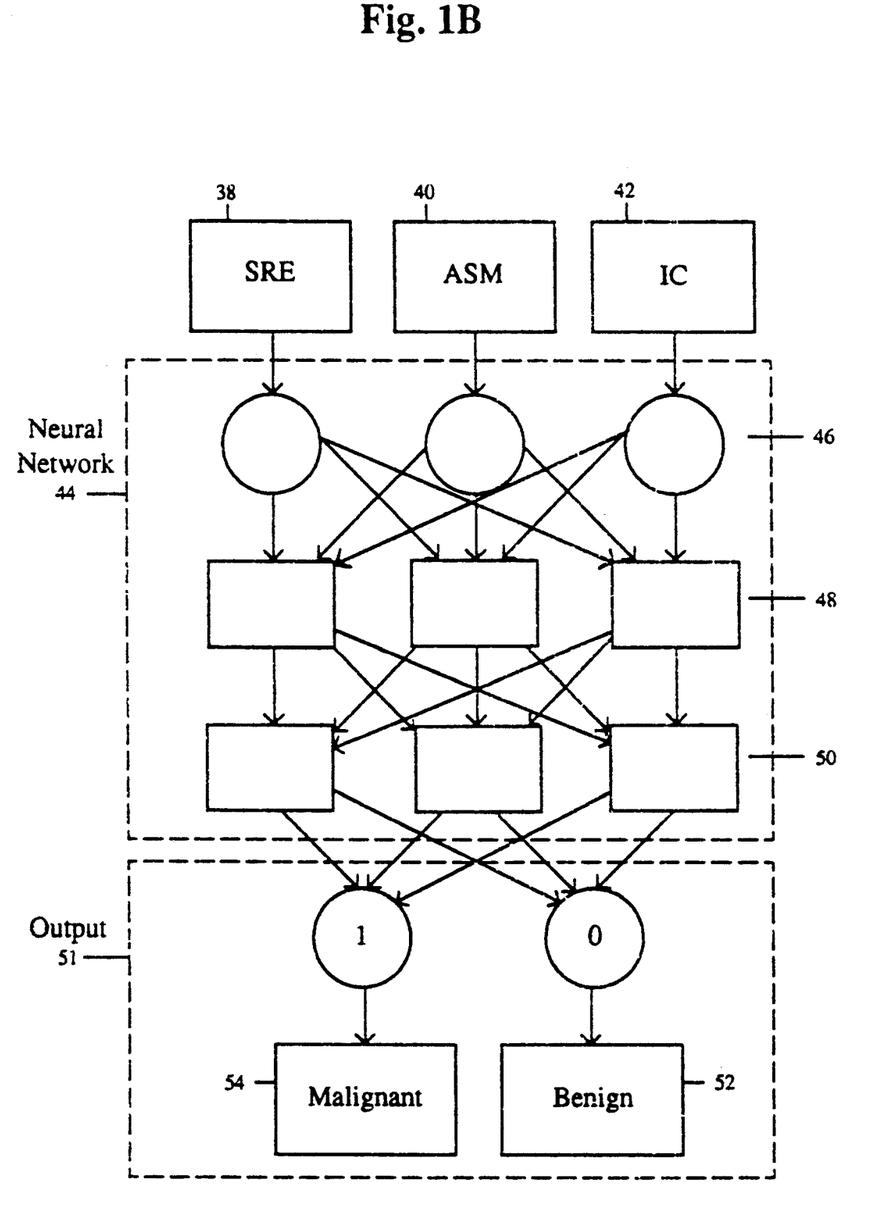

Neural network 44, illustrated in FIG. 1B, has an input layer 46 (to which features are presented), and an output layer 50 (giving the network's output), and one intermediate or "hidden" layer 48. Each layer has several processing elements, each of which is connected to some or all the elements in the adjacent layers. Each processing element typically receives inputs from the elements in the layer above (or the input data), calculates a weighted sum, and send its output (the result) to the next layer (or the network's output 50).

The output 51 from the neural network 44 of the present invention, comprises a range of values between 0 and 1, classifying the candidate tissue 16 as benign 52 or malignant 54. An arbitrary threshold, usually but not necessarily set at 0.5, is used to decide boarderline cases.

Figure 3:
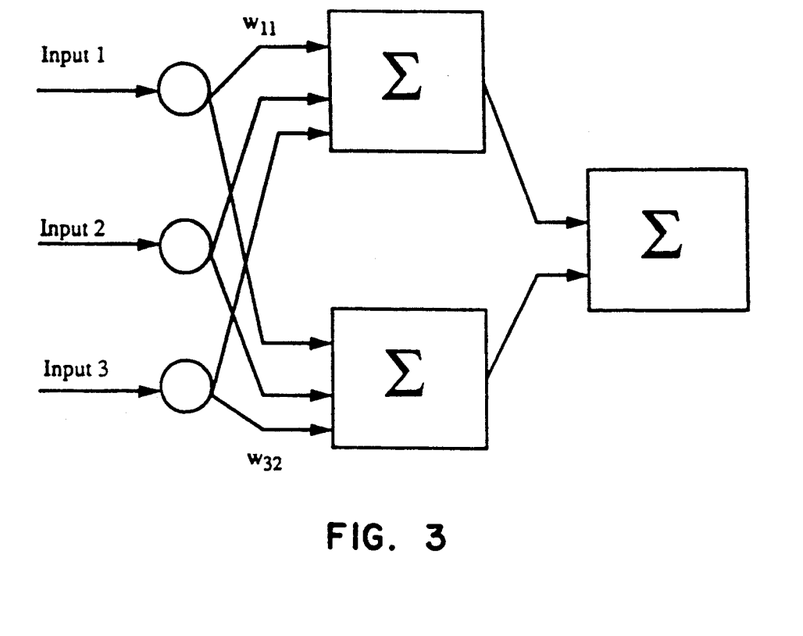
FIG. 3 is a schematic of the preferred and illustrated embodiment's fully connected back propagation neural network with three input nodes, two intermediate level nodes, and one output node illustrating the training of the network.

A brief description of neural networks, as proposed by P.D. Wasserman, *Neural Computing, Theory and Practice* (Van Nostrand Reinhold, pp. 43-58, 1989), is hereby incorporated by reference. The network selected for the preferred embodiment of the present invention is a three-layer back propagation network with three input nodes, two hidden nodes, and one output node, as illustrated in FIG. 3.

Training the Neural Network

In the training phase, desired outputs for given inputs are compared with actual outputs, and adjustments are made to the network's weights based on the differences. After repeating this for many presentations of many inputs, the network "learns" to produce the desired responses. When it can do this sufficiently well, it is deemed to be "trained," and its weights will contain encoded in their values information on mapping input data to outputs. Such networks usually generalize well on new input data (i.e., data not part of the training data 56) and give good results when presented with incomplete or noisy data.

Training a neural network on the available data can give unacceptable results because the large number of benign cases tend to dominate the few malignant ones, and many of the malignant cases are misclassified. The present invention overcomes this problem by biasing the network to place much greater importance on its performance with the benign cases. Two schemes are available to achieve this.

The first scheme is to replicate each of the malignant data points many times (10 times in the preferred embodiment) and present them to the network as if they are separate data points. Therefore, the training data of the present invention had 340 malignant cases (10×34 malignant cases) + 166 benign cases.

The second scheme, chosen for the preferred embodiment of the present invention, is termed "gap training." The network's output is constrained to be between 0 and 1, and in normal training it is told that the correct output is 0 for benign cases and 1 for malignant cases. The modification consisted of telling it that its output should be a much larger number than 1 for the malignant cases, even though it could never achieve this. Every time the network is presented with a malignant case during training, even if it classified it correctly, it will respond as if it had made a serious error and alter its decision boundary so as to attempt to better include that point on the malignant side. After some experimentation, using this approach with a gap coefficient of 6 provided to yield much faster convergence than replication (by 10 times) and more robust results as measured by jackknifing tests, discussed in more detail below.

Figure 4:
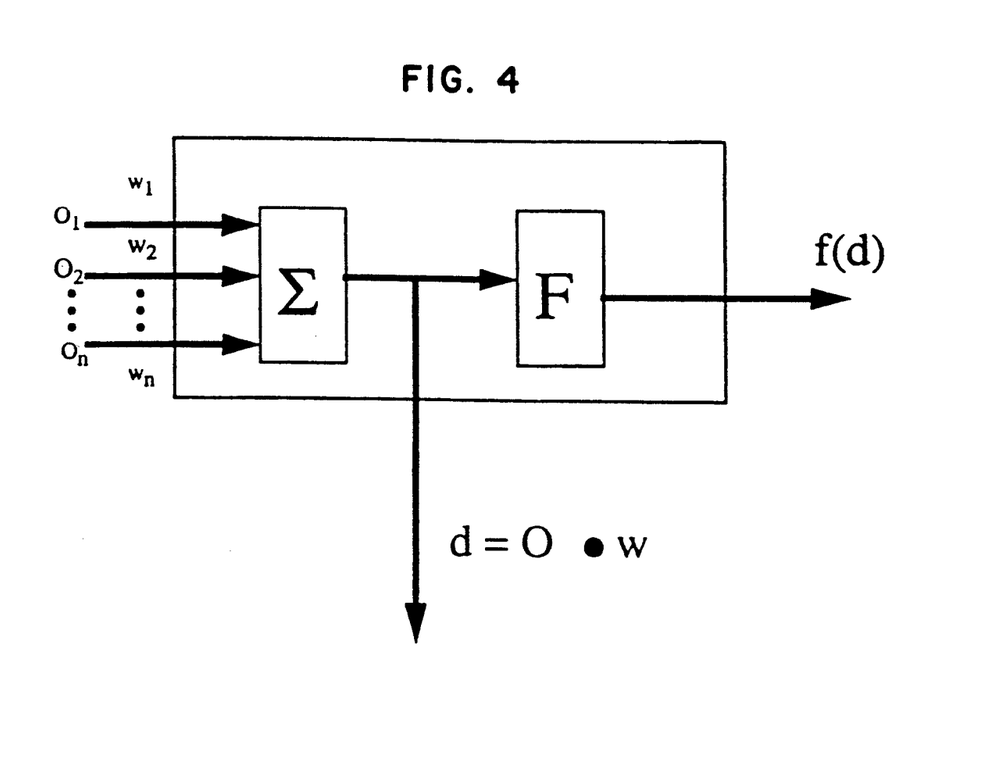
FIG. 4 is the neuron used as the fundamental building block for back propagation networks, where $f(d) = 1/(1 + \exp(-d))$.

The diagram of a typical computing node—also called neuron—used as the basic building block for back propagation networks is shown in FIG. 4. Following Wasserman's notation, the $ array multiplication is defined as the operation that when applied to two equal length n arrays A and B results in a new array C containing n elements, where the value of the "ith" element $c_i$ in C is $a_i b_i$, the product of the "ith" elements in A and B. An array of inputs A to the neuron, dollar multiplied to an array of weights B, results in an array C. The neuron then adds the weighted inputs, effectively producing a scalar multiplication of the presented array by the weight array, producing a signal d. After d is calculated, an "activation" function $f$ (typically a sigmoid) is applied to it, $$f(d) = 1/(1 + e^{-d}).$$

Sometimes called a logistic, or simply a squashing function, the sigmoid compresses the range of d so that $f(d)$ is between zero and one.

Figure 5:
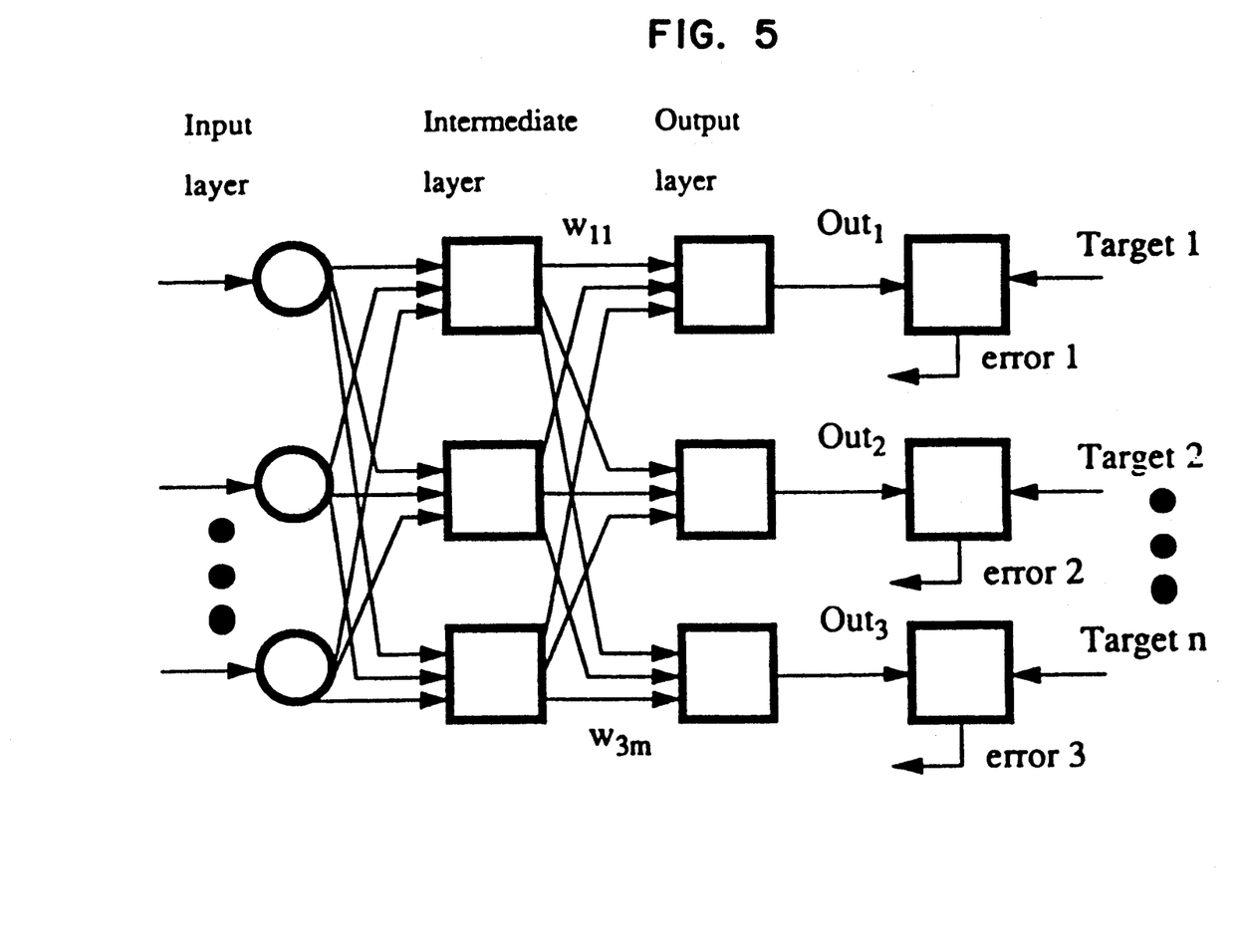
FIG. 5 is a two-layer back propagation network illustrating network training for the present invention.

The back propagation network is supervised, as illustrated in FIG. 5, in the learning stage because there is a target array (i.e., target data) of values to which the output of the network is compared.

This comparison is used to correct the values of the weights in the connections leading to the output layer, according to the following "delta" rule: After propagating the values of an input test to the output, the output of a neuron $f(d)$ is subtracted from its target value T (i.e., target data) to produce an error signal $E = T - f(d)$. This is multiplied by the derivative of the sigmoid $[f(d)(1-f(d))]$, (producing the value, $$\partial = f(d)[1-f(d)][T-f(d)].$$

Delta is then multiplied by the output &71 (d) from a feeding neuron k, the source neuron for the weight in question. This product is in turn multiplied by a training rate coefficient $\eta$ (typically 0.01 to 1) and the result is added to the weight. An identical process is performed for each weight proceeding from a neuron in the intermediate layer to a neuron in the output layer. The following equation illustrates this calculation $$\omega_{pq,k}(n+1) = \omega_{pq,k}(n) + \eta \partial_{q,k} f(d)_{p,j},$$

where $\omega_{pq,k}(n)$ is the value of a weight from neuron p in the hidden layer to neuron q in the output layer k at step n; n+1; $\partial_{q,k}$ is the value of delta for neuron q in the output layer k; and $f(d)_{p,j}$ is the value of $f(d)$ for neuron p in the hidden layer j.

Once the weights in the output layer have been altered, they can act as targets for the outputs of the hidden layer, changing the weights in the hidden layer following the same procedure as above. This way the corrections are back propagated to eventually reach the entered layer. After reaching the input layer, a new test is entered and forward propagation takes place again. This process is repeated until either a preset error E is achieved or a number of cycles N has been run.

It will be understood by those skilled in the art that the values of the weights can vary with a variety of factors. For example, a larger data set would allow better fine tuning of the neural network and affect both the quantity of weighting factors and their respective values. Further, the developing conditions as well as variations of the film used to create the digitized image 14 can affect image texture. Variability between ultrasound scanners 12 can affect the results of texture analysis, as well as variability introduced during digitization of the ultrasonogram. The size and accuracy of the learning set will affect overall specificity of the neural network. Therefore, weights must be developed for each system configuration according to the learning data available.

Learning Set Data Collection.

The population of learning data (i.e., feature and target data) utilized in the present invention included a cohort of 349 patients who had: 1) indeterminate masses on clinical examination and/or mammograms; 2) ultrasonographic examination of these masses; and 3) excisional biopsies of the masses. Results of ultrasonography and mammography were compared to results by surgical pathology for all operated patients. These 349 patients became a superset of the target population for the study. This superset included patients who were examined with either one of two different ultrasound machines. As the signals flow through the hardware of the different scanners, they are subjected to different processing steps that produce images which are similar but possibly different enough to affect the results of the texture analysis. Because of this consideration, only the set of patients that were scanned with one of the machines, a 7.5-MHz Ausonics® scanner with which most of the data were produced was utilized. Patients were also deleted from the cohort if their studies could not be located, a tumor was not identified on the ultrasonograms (a region of interest could not be taken), or the tumor was small (3 mm or less, so that no meaningful texture analysis could be done). Thus, 149 patients were excluded and the final cohort consisted of 200 patients between the ages of 14 and 93 years (mean, 54 ± 16 yr). Thirty-four patients had malignant tumors and 166 had benign tumors as determined by biopsy.

Testing (Jackknifing Method)

Tests done in the present invention with a jackknifing technique indicate that the neural network is able to generalize well with new cases. The following rules were applied to each malignant case in turn using the jackknifing method in the preferred embodiment:
1. Remove 1 malignant and 10 random benign cases from the total data set.
2. Train the network on the remaining data.
3. Run the resulting network on the removed cases and measure the accuracy, specificity, and sensitivity.

The network in the preferred embodiment of the present invention was trained for 20,000 presentations of data points randomly drawn from the learning set. In most cases this yielded a good separation of the learning data, with 100% of the malignant cases clearly identified as such and a good fraction of the benign cases (typically 40%) separated from these.

About 30% of the time this is not the case: one or two malignant cases in the learning set were misclassified. If this occurred, training continued for 50,000 or even 100,000 presentations until all the malignant cases were correctly classified.

With this approach, all the jackknifing tests delivered successful results. The malignant set was correctly classified, whereas a varying fraction of the benign samples (averaging 44 ± 3.9%, value ± SD) were classified as benign. This success verifies that the network can generalize well and correctly classify new malignant cases.

One lesson from the experimentation and well known in the literature is that it is possible to overtrain the networks so that they perform well on their learning set, but fail test sets. The success of the jackknifing tests of the present invention supports the conclusion that the network is not overtrain.

The classifier with two hidden layers can divide the feature space with no more than two hyperplanes. Even so, the results are better than with other classification methods. The effect of other scanners on these results is unknown. However, as time goes on, the images of various scanners are becoming more consistent. Results are expected at least as good if the method is applied to equipment-independent signals such as the appropriately processed and digitized radio frequency (RF) signal. The results realized with the present invention support what has been known in the image processing field for some time, that computer analysis of images can detect differences between images that the trained eye cannot. This principle can be applied elsewhere in ultrasonic biomedical image analysis.

The fact that the short run emphasis 38 is the best classifying feature suggests that the short range variations due to the increased vascularity of the cancerous tumors could be one underlying physical characteristic that is being mapped. Another possible physical characteristic could be the spatial distribution of the elastic modulus of dying cells intermixed with living tissue.

Overview of Neural Network Training and Operation

Figure 6:
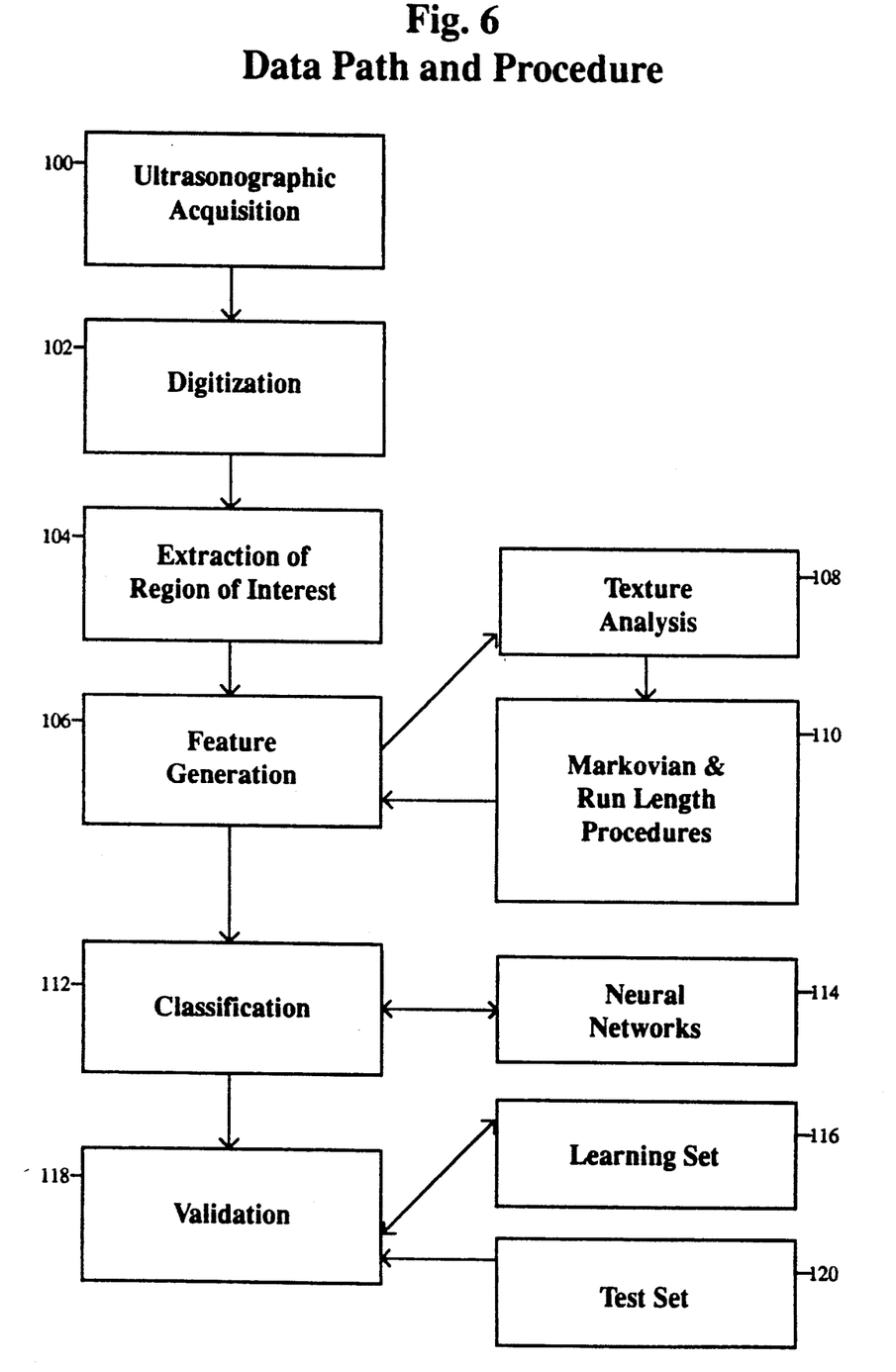
FIG. 6 is a flow chart of the data path and procedure for training and utilizing the neural network of the present invention.

An ultrasonagraphic image is acquired 100 for the population of patients, generating learning data for the neural network. These images are digitized 102 and a regions of interest are extracted 104. Feature generation 106 involves texture analysis 108 of the digitized images 102, using Markovian and run length procedures 110.

During the training phase, the actual classifications 112 by the neural network 114 are compared with the desired outputs from the learning set 116 data. Adjustments are made to the network's weights based on the difference between the two values. The goal of the training phase is to accurately separate breast ultrasonograms of benign tumors from a set of mammographically indeterminate tumors with a predicted high degree of sensitivity, thereby setting the values of the weights to be applied for the classification of the test set. Validation 118 occurs when the network produces the desired results with a high degree of sensitivity for the test set 120 of patient data.

In actual use, the present invention would perform texture analysis on the patient's digitized ultrasonogram utilizing the three features discussed above. The neural network would then classify the patient's candidate tissue as benign or malignant, utilizing the weights developed during the training phase.

The neural network of the present invention diagnosed the test cases in the training data with 100% sensitivity and about 40% specificity (compared with 0% specificity for the radiologist diagnosing the same set), thus potentially decreasing the number of unnecessary biopsies by 40% in patients with sonographically identifiable lesions. Tests performed with a jackknifing technique indicate that the network generalizes well to new cases.

While a particular embodiment has been described, it will be appreciated that modifications can be made without departing from the scope of the invention as defined in the appended claims. In particular, it will be recognized that it would be advantageous to collect the digitized image directly from the scanner, avoiding the data degradation that occurs when the image is transformed from digital to analog and then to digital again. It also would be of value to develop a scheme for feature generation and data classification by using an RF signal and to increase the number of features generated for use in the neural network.

I claim:

1. A method for distinguishing benign from malignant tumors in ultrasonic images of candidate tissue taken from a patient, comprising:

digitizing selected ultrasonic images from a plurality of patients generating an array of pixel intensity values;

entering into a computer said digitized ultrasonic images and target data based on excisional biopsy results for each of said patients where the candidate tissue is identified as malignant or benign;

locating and defining a region of interest in said digitized ultrasonic images, which includes substantially all of the candidate tissue and excludes substantially all normal tissue;

generating a first feature value from said arrays of pixels corresponding to an angular second moment of said pixel intensity values;

generating a second feature value from said arrays of pixels corresponding to an inverse contrast of said pixel intensity values;

generating a third feature value from said arrays of pixels corresponding to a short run emphasis of said pixel intensity values;

applying a set of weights to said first, second, and third feature values for generating network output values between an upper and lower value, whereby said output values tend toward said upper value when the candidate tissue is malignant and said output values tend toward said lower value when the candidate tissue is benign;

calculating a deviation between said output values with said target data; and altering said weights until said deviation is reduced to a predetermined value.

2. The method of claim 1 for distinguishing benign from malignant tumors in ultrasonic images of candidate tissue taken from a patient, further comprising the steps of increasing said target data above said upper value for malignant candidate tissue to increase the rate at which said altering step reduces said deviation to said predetermined value.

3. A method for distinguishing benign from malignant tumors in ultrasonic images of candidate tissue taken from a patient, comprising:

digitizing said ultrasonic image generating an array of pixel intensity values;

locating and defining a region of interest in said digitized ultrasonic image, which includes substantially all of the candidate tissue and excludes substantially all normal tissue;

generating a first feature value from said array of pixels corresponding to a angular second moment of said pixel intensity values;

generating a second feature value from said array of pixels corresponding to a inverse contrast of said pixel intensity values;

generating a third feature value from said array of pixels corresponding to a short run emphasis of said pixel intensity values; and applying a set of weights to said first, second and third feature values for generating network output values between an upper and lower value, whereby said output values tend toward said upper value when the candidate tissue is malignant and said output values tend toward said lower value when the candidate tissue is benign.

4. An apparatus for distinguishing benign from malignant tumors in ultrasonic images of candidate tissue taken from a patient, comprising:

means for digitizing selected ultrasonic images from a plurality of patients generating an array of pixel intensity values;

means for entering into a computer said digitized ultrasonic images and target data based on excisional biopsy results for each of said patients where the candidate tissue is identified as malignant or benign;

means for locating and defining a region of interest in said digitized ultrasonic images, which includes substantially all of the candidate tissue and excludes substantially all normal tissue;

first extraction means for generating a first feature value from said arrays of pixels corresponding to a angular second moment of said pixel intensity values;

second extraction means for generating a second feature value from said arrays of pixels corresponding to a inverse contrast of said pixel intensity values;

third extraction means for generating a third feature value from said arrays of pixels corresponding to a short run emphasis of said pixel intensity values;

an untrained neural network means coupled to said first, second and third feature value extraction means for determining a set of weights to said feature values for generating network output values between an upper and lower value, whereby said output values tend toward said upper value when the candidate tissue is malignant and said output values tend toward said lower value when the candidate tissue is benign;

means for calculating a deviation between said output values with said target data; and means for altering said weights until said deviation is reduced to a predetermined value.

5. The apparatus of claim 4 for distinguishing benign from malignant tumors in ultrasonic images of candidate tissue taken from a patient, further comprising means for increasing said target data above said upper value for malignant candidate tissue to increase the rate at which said means for altering reduces said deviation to said predetermined value.

6. An apparatus for distinguishing benign from malignant tumors in ultrasonic images of candidate tissue taken from a patient, comprising:

means for digitizing said ultrasonic image generating an array of pixel intensity values;

means for locating and defining a region of interest in said digitized ultrasonic image, which includes substantially all of the candidate tissue and excludes substantially all normal tissue;

first extraction means for generating a first feature value from said array of pixels corresponding to a angular second moment of said pixel intensity values;

second extraction means for generating a second feature value from said array of pixels corresponding to a inverse contrast of said pixel intensity values;

third extraction means for generating a third feature value from said array of pixels corresponding to a inverse contrast of said pixel intensity values;

a trained neural network means coupled to said first, second and third feature network means coupled to said first, second and third feature value extraction means for applying a set of weights to said feature values for generating network output values between an upper and lower value, whereby said output values tend toward said upper value when the candidate tissue is malignant and said output values tend toward said lower value when the candidate tissue is benign.

* * * * *

UNITED STATES PATENT AND TRADEMARK OFFICE
CERTIFICATE OF CORRECTION

PATENT NO. : 5,260,871
DATED : November 9, 1993
INVENTOR(S) : Victor Goldberg

It is certified that error appears in the above-identified patent and that said Letters Patent is hereby corrected as shown below:

In column 6, line 18, "data 56)" should read --data)--.

In column 7, line 15, "(producing" should read --producing--.

In column 7, line 18, ""&71 (d)" should read --f(d)--.

In column 12, line 24, delete "inverse contrast of said pixel intensity values;" and insert therefor --short run emphasis of said pixel intensity values; and--.

In column 12, lines 26 and 27, delete "network means coupled to said first, second and third feature" (second occurrence).

Signed and Sealed this

Twenty-first Day of June, 1994

Attest:

BRUCE LEHMAN

Attesting Officer      Commissioner of Patents and Trademarks